US008434492B2

(12) United States Patent  (10) Patent No.: US 8,434,492 B2
Jones  (45) Date of Patent: May 7, 2013

(54) VERTEBRAE SUPPORT DEVICE AND METHOD

(76) Inventor: Kevin D. Jones, Lake Worth, FL (US)

( * ) Notice: Subject to any disclaimer, the term of this patent is extended or adjusted under 35 U.S.C. 154(b) by 266 days.

(21) Appl. No.: 12/853,734

(22) Filed: Aug. 10, 2010

(65) Prior Publication Data
US 2012/0037163 A1  Feb. 16, 2012

(51) Int. Cl.
*A61G 15/00* (2006.01)
*A61N 1/00* (2006.01)
*A47C 20/00* (2006.01)
*B68G 5/00* (2006.01)

(52) U.S. Cl.
USPC .............. 128/845; 600/15; 5/630; 5/652

(58) Field of Classification Search .............. 128/845, 128/846, 870, 871, 133; 5/630, 731, 652; 606/240; D24/200
See application file for complete search history.

(56) References Cited

U.S. PATENT DOCUMENTS

| | | | | |
|---|---|---|---|---|
| 4,230,099 | A | * | 10/1980 | Richardson .................. 606/240 |
| 5,722,102 | A | * | 3/1998 | Summers ......................... 5/630 |
| 5,774,916 | A | * | 7/1998 | Kurhi .............................. 5/632 |
| D398,399 | S | | 9/1998 | Vincent et al. |
| 5,925,003 | A | | 7/1999 | Vincent et al. |
| 2002/0068888 | A1 | * | 6/2002 | Wang et al. .................... 601/136 |
| 2008/0092300 | A1 | * | 4/2008 | Joe et al. ........................... 5/655 |
| 2010/0236560 | A1 | * | 9/2010 | Rambo et al. ................. 128/845 |
| 2011/0041251 | A1 | * | 2/2011 | Ramer et al. ..................... 5/655 |

OTHER PUBLICATIONS

Spine-Worx website (http://www.spineworx.com/, http://www.spineworx.com/404557.html, http://www.spineworx.com/404565.html), accessed Dec. 1, 2012.
"Spine-Worx Alignment Therapy," Contour Living website (http://www.contourliving.com/p-64-spine-worx-spinal-alignment-therapy.aspx), accessed Dec. 1, 2012.
"How the True Back Works," True Back website (https://www.trueback.com/how-it-works.php), accessed Dec. 1, 2012.
Relax Mate Orthopedic Back Support advertisement, IB3 Health website (http://www.ib3health.com/products/MiniMassager/PlasticMassageTool/RelaxMateBackStretcher.asp), accessed Dec. 1, 2012.
Back Magic website (http://www.backmagicworks.com/), accessed Dec. 1, 2012.

(Continued)

*Primary Examiner* — Patricia Bianco
*Assistant Examiner* — Tarla Patel
(74) *Attorney, Agent, or Firm* — Spilman Thomas & Battle, PLLC

(57) ABSTRACT

A vertebrae support device. The vertebrae support device includes a base made of a yielding material and having resting surface, a rail side, a first lateral side a second lateral side, a head end, and a foot end. A first rail extends from the rail side of the base from the resting surface of the base and adjacent the first lateral side and having a rounded surface opposite the base. A second rail extends from the rail side of the base from the resting surface of the base and adjacent the second lateral side and having a rounded surface opposite the base, a trough depending between the first and second rails and toward the base at least one inch. A headrest is formed on the head end of the base.

11 Claims, 2 Drawing Sheets

OTHER PUBLICATIONS

"North American Healthcare Arched Back Stretcher," Quantum Butterfly Effect website (http://www.quantum-health-scio-biofeedback.com/backstretcher.htm), accessed Dec. 1, 2012.

Freedom Back product page, TheHealthyBack Institute website (http://www.losethebackpain.com/freedomback.html), accessed Dec. 1, 2012.

"The Passive Motion Back Pain Reliever," Hammacher Schlemmer website (http://www.hammacher.com/Product/Default.aspx?sku=79124&refsku=77890), accessed Dec. 1, 2012.

Issachar Gilad and Moshe Nissan, "Sagittal evaluation of elemental geometrical dimensions of human vertebrae," J. Anat. (1985), 143, 115-120.

* cited by examiner

VERTEBRAE SUPPORT DEVICE AND METHOD

CROSS-REFERENCE TO RELATED APPLICATIONS

Not Applicable

STATEMENT REGARDING FEDERALLY SPONSORED RESEARCH

Not Applicable

THE NAMES OF THE PARTIES TO A JOINT RESEARCH AGREEMENT

Not Applicable

INCORPORATION-BY-REFERENCE OF MATERIAL ON DISC

Not Applicable

BACKGROUND OF THE INVENTION

It has been suggested that good posture improves health. It has further been suggested that extending the shoulders toward the back of the body provides natural enlargement of space in which body organs operate so that, for example, lungs can expand more readily, thereby moving greater quantities of air and reducing respiration rate, and that external pressure on the heart is reduced by such a posture, thus creating a possibility for greater pumping volumes and the potential for reducing heart rate, and particularly resting heart rate.

It has also been suggested that acupressure, or pressure applied to portions of the body, can promote relaxation and wellness.

Accordingly, it is believed that embodiments of the present invention may beneficially provide better posture.

It is furthermore believed that embodiments of the present invention may beneficially provide improved bodily function.

It is also believed that embodiments of the present invention may beneficially provide promote relaxation.

It is furthermore believed that embodiments of the present invention may beneficially provide improved physical wellness.

It is also believed that embodiments of the present invention may beneficially provide improved musculoskeletal function.

It is also believed that embodiments of the present invention may beneficially provide improved psychological function.

SUMMARY OF THE INVENTION

Embodiments of apparatuses, systems, and methods for forming and using a vertebrae support device are provided herein.

In accordance with one embodiment of the present invention, a vertebrae support device is provided. The vertebrae support device includes a base made of a yielding material and having a resting surface, a rail side, a first lateral side a second lateral side, a head end, and a foot end. A first rail extends from the rail side of the base from the resting surface of the base and adjacent the first lateral side and having a rounded surface opposite the base. A second rail extends from the rail side of the base from the resting surface of the base and adjacent the second lateral side and having a rounded surface opposite the base. A trough depends between the first and second rails and toward the base. One or both of a cervical rest and a head rest may be formed on the head end of the base if desired.

In accordance with another embodiment of the present invention, a method of using a vertebrae support device is provided. In that method, a resting surface of the vertebrae support device may be disposed on a floor or other flat horizontal surface. A person may lie or be otherwise disposed on the rails of the vertebrae support device with the back of the person against the rails. The muscles disposed along each side of the vertebrae column of the person may thus be supported on the rails, while the vertebrae column of the person may extend into the trough of the vertebrae support device and may, thereby, be unsupported. The muscles in contact with the vertebrae support device may rest on the rails equidistant from the vertebrae column such that the vertebrae column is centered between the rails and the vertebrae column is centered over the trough. The shoulders of the person may fall back along first and second lateral sides and of the vertebrae support device, particularly if the person is lying on the vertebrae support device while the vertebrae support device is resting on a substantially horizontal surface. In this way, the vertebrae support device may apply an acupressure type of therapy along at least two medial planes of the body. Muscles in the neck of the person may rest on a cervical support portion of the vertebrae support device and the head of the person may rest on a head rest. Thus the cervical, thoracic and lumbar portions of the vertebrae column of the person lying on the vertebrae support device are unsupported in a trough between the first rail and the second rail and the neck of the person lying on the vertebrae support device.

Other embodiments, which may include one or more parts of the aforementioned method or systems or other parts, are also contemplated, and may thus have a broader or different scope than the aforementioned method and systems. Thus, the embodiments in this Summary of the Invention are mere examples, and are not intended to limit or define the scope of the invention or claims.

Accordingly, the present vertebrae support device provides solutions to the shortcomings of prior vertebrae support devices. Those of ordinary skill in the art will readily appreciate, therefore, that other details, features, and advantages will become further apparent in the following detailed description of the preferred embodiments.

BRIEF DESCRIPTION OF THE DRAWINGS

The accompanying drawings, which are incorporated herein and constitute part of this specification, include one or more embodiments of the invention, and together with a general description given above and a detailed description given below, serve to disclose principles of embodiments of pulsation attenuation devices and networks.

DETAILED DESCRIPTION OF THE INVENTION

Figure 1:
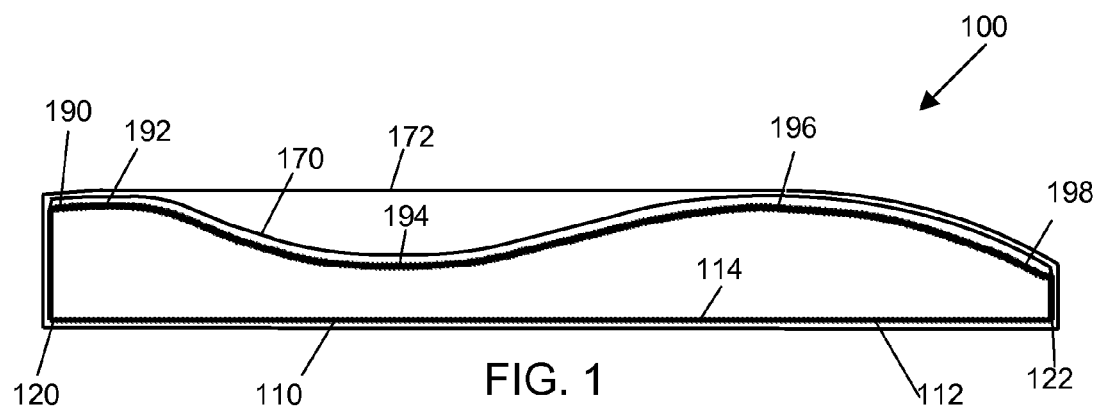
FIG. 1 illustrates a side view of an embodiment of a vertebrae support device.
Figure 2:
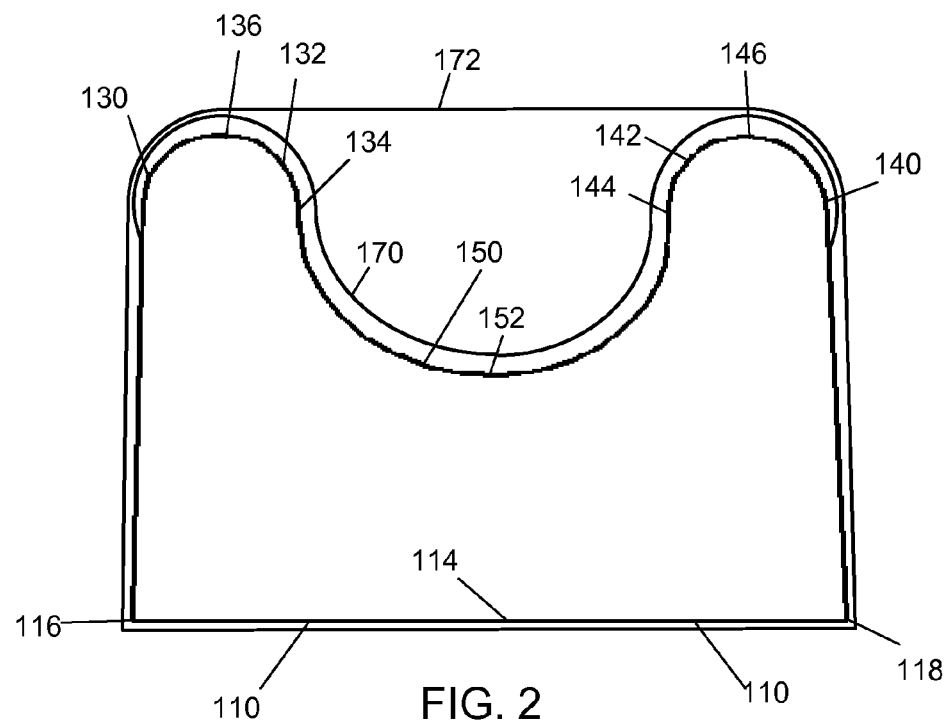
FIG. 2 illustrates an end view of the embodiment of the vertebrae support device illustrated in FIG. 1.

FIG. 1 illustrates a side view of an embodiment of a vertebrae support device 100 of the present invention and FIG. 2 illustrates an end view of the vertebrae support device 100 of FIG. 1. The vertebrae support device 100 includes a base 110, first and second rails 130 and 140 extending from the base, and a trough 150 positioned between the first and second rails 130 and 140.

The base 110 may be made of a yielding material such as polyurethane foam or foam rubber latex that is compressible when weight is applied to it and uncompressible when the weight is removed. Any materials that are resiliently elastic, springy, or that provide padding for the person disposed on the vertebrae support device 100 may be considered yielding for the purposes of this invention and may be a suitable material for manufacture of the base 110. Alternately, the base 110 may be made of wood, metal, plastic, fiberglass, natural rubber, or synthetic rubber. The vertebrae support device 100 may have a length as short as approximately 20 inches, for example for children and shorter people, and a length as long as approximately 28 inches to properly fit body sizes for large, tall, or obese individuals.

The base 110 illustrated in the embodiment of FIG. 1 includes a resting surface 112, a rail side 114, a first lateral side 116, a second lateral side 118, a head end 120, and a foot end 122. That embodiment includes a cervical rest or support 192 on the rail side 114, toward the head end 120 and a headrest 190 at the head end 120. The cervical rest 192 and headrest 190 may also be made of yielding materials, as described in connection with the base 110, and may serve to permit the neck of a user to rest on the cervical rest 192 and the head of the user to rest on the headrest 190 when the body of the user is resting on the vertebrae support device 100. The cervical rest 192 may be formed separately or as part of the base 110 and the headrest 190 may also be formed separately or as part of the base 110.

The rails 130 and 140 may extend from the rail side 114 of the base 110. The first rail 130 may furthermore extend from the first lateral side 116 of the base 110 and the second rail 140 may extend from the second lateral side 118 of the base 110. The first and second rails 130 and 140 may furthermore be positioned parallel to one another.

The rails 130 and 140 may also be formed of a yielding material, as described in connection with the base and the rails 130 and 140 may also be formed separately or as part of the base 110. Alternately, the rails 130 and 140 may be formed of a rigid or semi-rigid material or any of the alternate materials listed as materials that may be used in the base 110.

Each rail 130 and 140 may include a rounded surface 132 and 142, respectively, extending from the base 110. Each rounded surface 132 and 142 may have a width of approximately three-quarters of an inch at the rail bases 134 and 144, respectively, of each rounded surface 132 and 142. The centers of the rail bases 136 and 146 of the rails 130 and 140 may furthermore be positioned about two and three-quarters inches apart with the trough 150 positioned there between.

In an embodiment of a vertebrae support device 100, the first rail 130 extends from the first lateral side 116 of the base 110 to its rounded surface 132. The distance from the vertebrae support device 100 base 110 to the base 134 of the rounded surface 132 is about ten inches and at least six and one half inches. That height permits the shoulders of a person lying or otherwise disposed upon the vertebrae support device 100 to roll backward a sufficient distance to aid in the extension of that person's back.

The trough 150 may run the length of the vertebrae support device 100 and medial to the rails 120 and 130. The trough 150 may be arcuate transverse to the length of the vertebrae support device 100 and between the first lateral side 116 and second lateral side 118 and may be formed as a wave along the length of the trough 150 between the rails 130 and 140. The bottom 152 of the trough 150 may follow the wave of the rails 130 and 140 lying a consistent distance of at least one inch below the tops of the rounded surfaces 132 and 142 of the rails 130 and 140.

In the embodiment of the vertebrae support device 100 illustrated in FIGS. 1 and 2, the shape of the trough 150 between the lateral sides 116 and 118 of the vertebrae support device 100 may be a graduated concave curve attached to a reversely graduated convex curve on each side, wherein the reversely graduated convex curve forms the rails 130 and 140. The trough 150 may follow at a fixed or nearly fixed distance from the rails 130 and 140 along the length of the vertebrae support device 100 from the head end 120 of the vertebrae support device 100 to the foot end 122 of the vertebrae support device 100. The shape of the rails 130 and 140 and trough 150 along the length of the vertebrae support device 100 may, in an embodiment, form a headrest 190 at the head end 120, adjacent a cervical rest 192, followed by a first depression 194, a rise 196, and a second depression 198 extending to the foot end 122 of the vertebrae support device 100.

Figure 3:
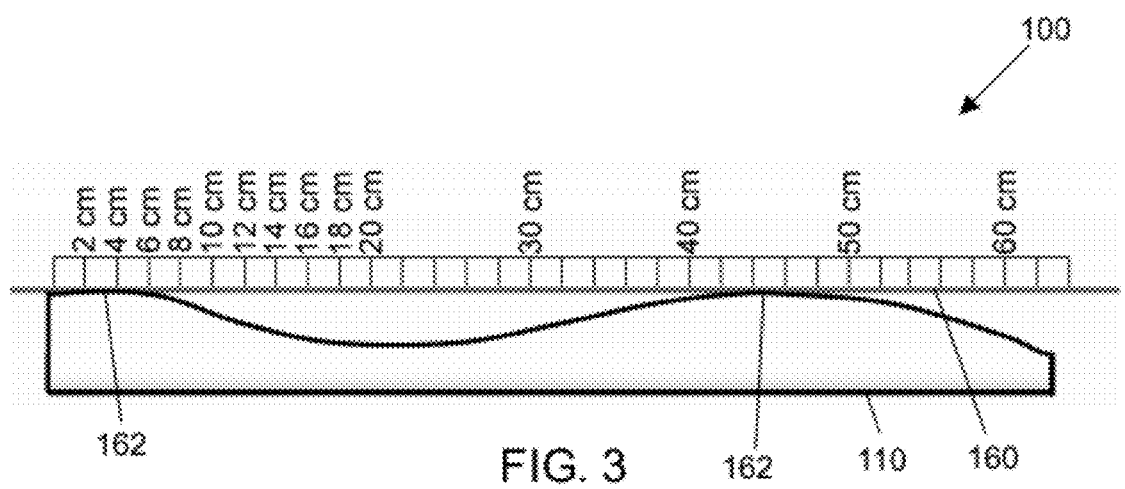
FIG. 3 illustrates a side view of an embodiment of a vertebrae support device with markings at two-centimeter increments along the length of the vertebrae support device.

In one embodiment of the vertebrae support device 100, the shape of the trough 150 from the head end 120 to the foot end 122 of the vertebrae support device 100 may be as described in Table 1, in which an actual or simulated 25 inch long (from head end 120 to foot end 122) vertebrae support device 100 was placed on a flat, horizontal surface. Next, as illustrated in FIG. 3, measurements were made from a horizontal plane 160 formed along the highest points of the rails 130 and 140 to the tops 162 of the rails 130 and 140 at two centimeter increments along the length of the vertebrae support device 100. Table 1 indicates that distance from the highest points of the rails 130 and 140 to the tops 162 of the rails 130 and 140 at two centimeter increments along the length of the vertebrae support device 100.

TABLE 1

| Horizontal Plane Mark (cm) | Distance from Horizontal Plane (cm) | Surface Angle (degrees) |
|---|---|---|
| 2 | 0.0 | 0 |
| 4 | 0.0 | 3 |
| 6 | 0.2 | 7 |
| 8 | 0.5 | 10 |
| 10 | 0.9 | 13 |
| 12 | 1.4 | 15 |
| 14 | 2.0 | 15 |
| 16 | 2.5 | 11 |
| 18 | 2.8 | 6 |
| 20 | 2.9 | 3 |
| 22 | 3.0 | 0 |
| 24 | 2.9 | 3 |
| 26 | 2.8 | 4 |
| 28 | 2.6 | 9 |
| 30 | 2.2 | 11 |
| 32 | 1.8 | 13 |
| 34 | 1.3 | 13 |
| 36 | 0.9 | 11 |
| 38 | 0.5 | 10 |
| 40 | 0.2 | 7 |
| 42 | 0.0 | 1 |
| 44 | 0.1 | 3 |
| 46 | 0.2 | 6 |

In operation, the trough 150 provides an area medial to the rails 130 and 140 in which a person's vertebrae column, at least the transverse process segment of each vertebrae, may extend into the trough 150 when the person is lying or otherwise positioned upon the rails 130 and 140. For example, when the vertebrae support device 100 is resting on a floor or other generally horizontal surface with a person lying in a relaxed state with the lateral portions of the person's back on each side of the vertebrae column resting comfortably on the rails 130 and 140, the vertebrae column of the person may settle downward under the force of gravity into the trough 150.

In an embodiment, such as shown in FIGS. 1 and 2, the vertebrae support device 100 may include a padding 170 that may be disposed at least partially on the rails 130 and 140. The padding may be made of a polyurethane foam or other soft and compressible material, or may be made of another padding material or materials.

In an embodiment, such as shown in FIGS. 1 and 2, the vertebrae support device 100 may include a cover 172. The cover may surround the base 110 and rails 130 and 140. The cover may be formed of any desired material or materials, such as a soft and/or waterproof or water resistant material. In various embodiments, the cover may be formed of a vinyl or leather, for example. The cover may include a zipper or other self-fastening device such that the cover can completely contain the rest of the vertebrae support device 100, that is, the portion including the base 110 and rails 130 and 140 (or possibly the rest of the vertebrae support device 100 other than the headrest 190 and cervical rest 192 if the headrest 190 and cervical rest 192 are included and formed separately from the base 110). In that embodiment, the cover may be "zipped around" the rest of the vertebrae support device 100 after the rest of the vertebrae support device 100 (with or without the headrest 190 and cervical rest 192) is disposed therein.

Manufacturing of the vertebrae support device 100 may be accomplished by cutting, molding, or otherwise forming the base 110 from an appropriate material, such as polyurethane foam. The rails 130 and 140 may also be cut, molded, or otherwise formed using, for example dies and a plastic thermo-molding process and attaching the rails 130 and 140 to the base 110 by, for example, gluing the rails 130 and 140 to the base 110, and attaching, for example by gluing, the padding material over the rails 130 and 140.

A method of promoting scapular retraction is further provided. In that method, the resting surface of the vertebrae support device 100 is disposed on a floor or other surface. A person then lies or is otherwise disposed on the rails 130 and 140 of the vertebrae support device 100 with the back of the person against the rails 130 and 140. The muscles disposed along each side of the vertebrae column of the person are thus supported on the rails 130 and 140, while the vertebrae column of the person extends into the trough 150 of the vertebrae support device 100 and may, thereby, be unsupported. The muscles in contact with the vertebrae support device 100 may rest on the rails 130 and 140 equidistant from the vertebrae column such that the vertebrae column is centered between the rails 130 and 140 and the vertebrae column is centered over the trough 150. The shoulders of the person may fall back along the first and second lateral sides 116 and 118 of the vertebrae support device 100, particularly if the person is lying on the vertebrae support device 100 while the vertebrae support device 100 is resting on a substantially horizontal surface. In this way, the vertebrae support device 100 may apply an acupressure type of therapy along a medial plane of the body.

The muscles supported on the rails 130 and 140 may include intertransversarii muscles, which facilitate movement between the individual vertebrae, and multifidus spinae muscles, which facilitate the movement of the spine as a whole. Such support may cause the vertebrae column to be suspended above the surface of the vertebrae support device 100 in the area of the trough 150, thus permitting the vertebrae column to hang from the muscles supported on the rails 130 and 140, and the permitting the shoulders to hang downward along the first and second lateral sides 116 and 118 of the vertebrae support device 100. Such a position may permit increased fluid movement around the spinal column, enhance relaxation and recovery after physical activity, and promote alignment of the vertebrae column.

Figure 4:
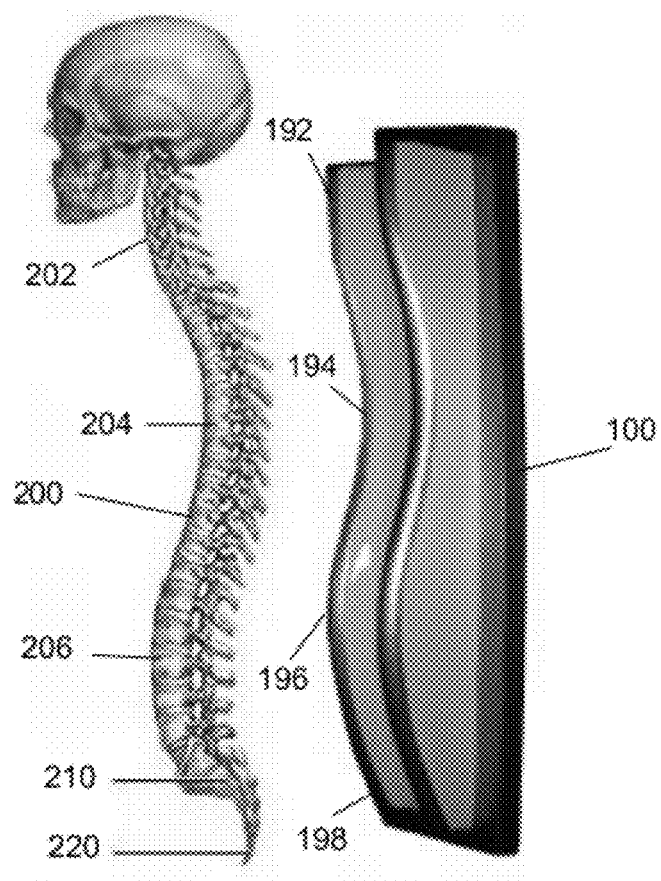
FIG. 4 illustrates a human spine adjacent another embodiment of a vertebrae support device.

FIG. 4 illustrates a human spine 200 adjacent a vertebrae support device 100. The human spine 200 illustrated follows a natural curve for a human spine 200. Viewed from the side as illustrated in FIG. 4, the human spine 200 includes cervical and lumbar sections having a lordotic, or slightly concave curve, and a thoracic section having a kyphotic, or gentle convex curve. As may be seen in FIG. 4, the neck may rest on the cervical rest or support 192 of the vertebrae support device 100 and the head may rest beyond the cervical rest 192, while the cervical spine 202 lies within the trough 150 created between the rails 130 and 140. The thoracic spine 204 lies in the trough 150 formed between the rails 130 and 140 along the first depression 194, and the lumbar spine 206 lies in the trough 150 formed between the rails 130 and 140 along on the rise 196 and second depression 198.

The natural curves of the human spine 200 are thought to be important and to provide strength and resilience to the body. The shape of the human spine 200 is thought to absorb shock and facilitate a full range of motion throughout the spinal column. Use of the vertebrae support device 100 is thought to provide alignment to the human spine 200 and to support the human spine in a proper alignment. Use of the vertebrae support device 100 is also thought to provide acupressure to relieve stress in the muscles in the area of the human vertebrae column.

While the present invention has been disclosed with reference to certain embodiments, numerous modifications, alterations, and changes to the described embodiments are possible without departing from the scope of the present invention, as defined in the appended claims. Accordingly, it is intended that the present invention not be limited to the described embodiments, but that it have the full scope defined by the language of the following claims, and equivalents thereof.

The invention claimed is:

1. A vertebrae support device, comprising:
   a base made of a yielding material and having a resting surface, a rail side, a first lateral side, a second lateral side, a head end, and a foot end;
   a first rail extending from the rail side of the base to a top at least six and one half inches from the resting surface of the base and adjacent the first lateral side and having a rounded surface opposite the base; and
   a second rail extending from the rail side of the base to a top at least six and one half inches from the resting surface of the base and adjacent the second lateral side and having a rounded surface opposite the base, the first rail and second rail each further including a rise;
   a trough depending between the first and second rails toward the base; and
   a cervical rest and a headrest formed on the head end of the base;
   wherein at least one of the cervical rest and the headrest has a height at least equal to a height of each rise.

2. The vertebrae support device of claim 1, the first rail being parallel to the second rail.

3. The vertebrae support device of claim 1, the first rail and the second rail being made of a yielding material.

4. The vertebrae support device of claim 1, wherein the trough is arcuate transverse to the length of the vertebrae support device.

5. The vertebrae support device of claim 1, the trough having a bottom and the bottom of the trough being a consistent distance below the top of the first and second rails.

6. The vertebrae support device of claim 5, wherein the consistent distance is at least one inch.

7. The vertebrae support device of claim 1, the first rail and the second rail each forming a first depression and a second depression.

8. The vertebrae support device of claim 1, further comprising a padding material disposed at least partially on the first rail and the second rail.

9. The vertebrae support device of claim 1, further comprising a cover containing the base, the first rail, and the second rail.

10. A vertebrae support device, comprising:
   A base formed of a yielding material and having a resting surface, a rail side, a first lateral side, a second lateral side, a head end, and a foot end;
   A first rail extending from the rail side of the base to a top at least six and one half inches from the resting surface of the base and adjacent the first lateral side, the first rail having a rounded surface opposite the base;
   A second rail extending from the rail side of the base to a top at least six and one half inches from the resting surface of the base and adjacent the second lateral side, the second rail having a rounded surface opposite the base, the first rail and second rail each further including a rise;
   an arcuate trough formed between the first and second rails and descending at least one inch from the top of the first and second rails, the trough providing an area to allow each transverse process segment of a vertebrae of a person positioned on the rails to extend into the trough;
   a headrest formed on the head end of the base; and
   a cervical rest formed adjacent the head rest;
   wherein at least one of the cervical rest and the headrest has a height at least equal to a height of each rise.

11. The vertebrae support device of claim 1, the trough providing an area to allow a transverse process segment of a vertebra of a person positioned on the rails to be positioned between the rails.

* * * * *